United States Patent [19]

Dreyer

[11] 4,108,972

[45] * Aug. 22, 1978

[54] IMMUNOLOGICAL REAGENT EMPLOYING RADIOACTIVE AND OTHER TRACERS

[76] Inventor: William J. Dreyer, 2369 Highland, Altadena, Calif. 91001

[*] Notice: The portion of the term of this patent subsequent to Dec. 10, 1991, has been disclaimed.

[21] Appl. No.: 631,378

[22] Filed: Nov. 12, 1975

Related U.S. Application Data

[63] Continuation-in-part of Ser. No. 451,485, Mar. 15, 1974, abandoned.

[51] Int. Cl.² ............... A61K 43/00; G01N 33/16
[52] U.S. Cl. .......................... 424/1; 23/230 B; 250/303; 424/8; 424/12
[58] Field of Search ............. 424/1, 8, 12; 23/230 B; 252/301, 1 R; 250/303

[56] References Cited

U.S. PATENT DOCUMENTS 3,853,987 12/1974 Dreyer ........................... 424/1
3,904,367 9/1975 Golibersuch .................. 23/230 B Primary Examiner—Benjamin R. Padgett
Assistant Examiner—Christine M. Nucker
Attorney, Agent, or Firm—William W. Haefliger

[57] ABSTRACT

A broad new class of reagents permits extremely sensitive and specific assay for, or chemical separation of, a broad range of biological and nonbiological substances. Each reagent consists of a suspension of microscopic carrier material particles, each particle bearing (1) tracer material - fluorescent, radioactive or otherwise - and (2) a coating of biological homologue, that is, antibody, antigen, or portions or equivalents thereof, for the substance whose assay is desired.

The latter substance if introduced into the suspension links the particles together in pairs or clumps, which may be sensitively and accurately detected by monitoring the tracer. The carrier is preferably partially hydrolyzed polyacrylamide resin, or in appropriate applications acrylic acid and other derivatives thereof, and other polymers including agar, and the coupling effected by covalent bonding. Other embodiments, including various mechanical forms of carrier, for greater ease of handling and separation, are also described.

21 Claims, 1 Drawing Figure

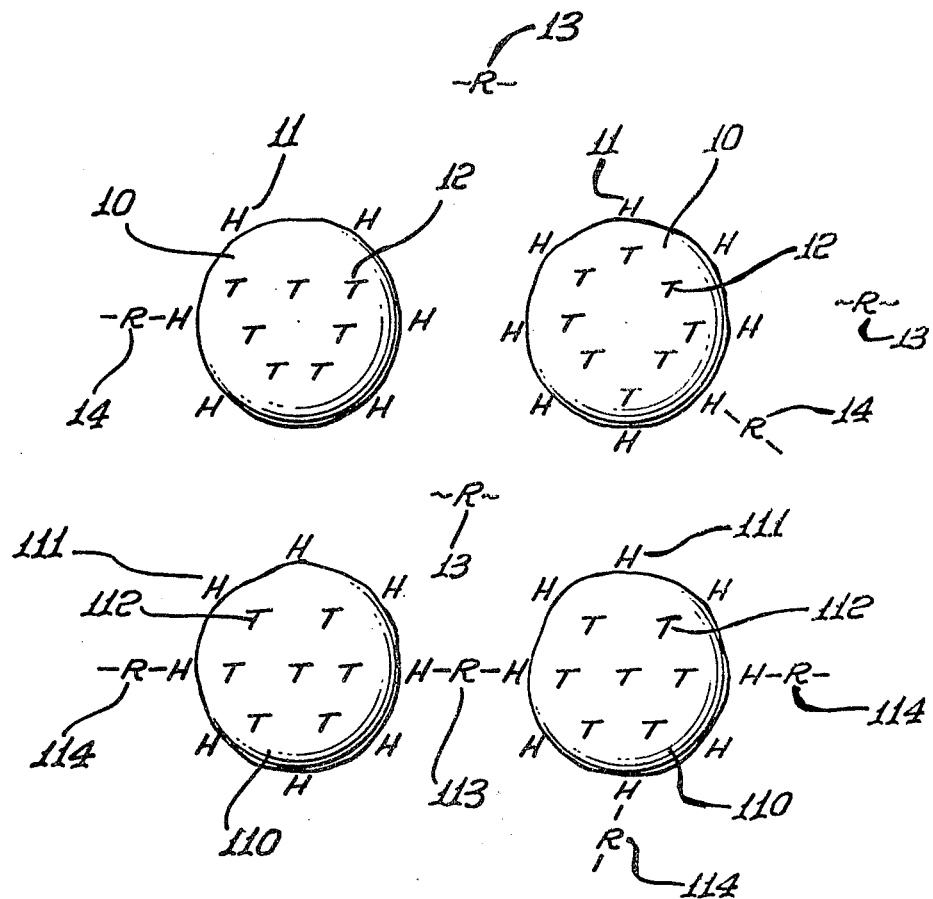

IMMUNOLOGICAL REAGENT EMPLOYING RADIOACTIVE AND OTHER TRACERS

BACKGROUND OF THE INVENTION

This application is a continuation-in-part of my pending application Ser. No. 451,485 filed Mar. 15, 1974, now abandoned and entitled "Immunological Reagent".

The present invention is directed to the concept that the immune reaction and its products can be used for chemical separations and assays. This concept is for example implemented by causing an organism (often a mammal, such as a rabbit, mouse or horse) to generate antibody to a particular substance—a substance which is to be the object of an assay or separation.

The antibody thus formed may be used to "seek" further quantities of the particular substance which produced it, and the resulting reactions may be used in a vast variety of ways — to precipitate or agglutinate the particular substance out of solution or suspension, thus indicating its presence qualitatively or quantitatively while effecting a separation; or to couple the particular substance to tracer material, or solid or semi-solid material, pre-attached to the antibody. Alternately, if antibody is to be detected, for example in the diagnosis of certain known forms of cancer, the antigen to such antibody is first isolated, then used in a manner completely analogous to that in which antibody may be used, as described above, that is to "seek" quantities of the "particular substance", in this instance, antibody. Because of this duality between antigen and antibody, I have used the term "immunological homolog", as defined below to represent either an antigen or antibody or immunological reactive portions or equivalents thereof.

Some of these applications have been known for years but are greatly facilitated, and rendered amenable to automation, by the present invention; others of these applications have been conceived of only in the light of the present invention, and would not have been at all practical or meaningful previously. To suggest the enormous power of the instant invention, there are listed below a number of its applications.

This listing represents only a few of the potentialities of immune assay and separation, which are unrealizable or imperfectly realizable without the present invention:

(1) location, separation and measurement of cholesterol, hormones, viruses and other such antigens or their antibodies such as anti-virus antibodies, in serum;

(2) quantitative assay for enzymes by their presence — not merely by an indirect measure of their activity;

(3) assessment of the character and/or effectiveness of an organism's immune-system response, or of its suppression — as, for example, preparatory to transplant surgery; and (4) assay for an almost unlimited variety of miscellaneous substances — including even omnipresent biological materials such as steroids — by using techniques involving attachment of such low-molecular-weight molecules to proteins.

Not only research analyses and separations, but clinical and other routine uses are contemplated.

It is felt that great advances in medical science and practice hinge on the application of the immune mechanisms to these listed areas and others; and that such application in turn hinges on the present invention, which at once renders immunological separations and assays significantly more sensitive, reproducible, accurate, convenient and amenable to automation than heretofore possible.

Radioactive, fluorescent, free radicals (spin labels), and enzyme molecules, and other "tracers" or "tags" are used extensively in biochemistry. Other tracers such as atoms which may produce distinctive fluorescence when exposed to X-rays, also paramagnetic atoms and molecules have been suggested. It can be seen that the range of possibilities is very wide. Immunology is one of the areas in biochemistry in which tracers have been widely used. However, in the context of the present invention they are used in a way which is believed novel and unobvious.

Conventionally, tracers are coupled directly to one of the molecules or cells of interest in a particular reaction or assay; sometimes tracers are coupled via intermediaries which simply serve to supply appropriate chemical combining properties for both the active component and the tracer.

Radioactive tracers have the disadvantage that their radioactive decay cannot be "turned off or on" at will. Thus if high activity, to attain high sensitivity, is desired, the tagged reagent is continually bombarded from the time of its manufacture, with ionizing and destructive radiation. Not only does the radioactivity itself have limited life, but the reagent steadily deteriorates, further limiting the useful life and increasing the probability of non-specific reactions. Radioactive tracers may therefore be quite unusable, for applications of the sort considered here, in remote locations.

In addition, as is well known, radioactive substances are dangerous. Persons who handle them are required by common sense and by law to have special training. Furthermore their detection requires very expensive, special purpose instrumentation.

They give high sensitivity (though not nearly so high as certain fluorescent label molecules), and while widely used for this reason their applications have been limited mainly to well-equipped research laboratories.

Fluorescent tracers yield overall reaction-detection sensitivities which, though a great deal better than those obtainable with radioactive and other sorts of tags, have still heretofore left much to be desired. Nevertheless, tracers have been used extensively for localization of specific constituents at the outer surfaces of cells, or within cells — that is, in cytology. Fluorescent tracer work with immune reactants, generally known as "immuno-fluorescence", has heretofore been put to use primarily in cytology. Since cells are in a sense particles, the distinction between immuno-fluorescence and parts of the present invention is essential. In immuno-fluorescence the biological cells ("particles") are themselves the objects of a screening survey; while in the present invention the particles (or other carrier forms) are part of a chemical tool used for assays and separations of other substances, as explained later.

Fluorescent tracers have also been used in other immunological work — but in such other instances the tracer molecules have simply been added or attached to immune reagent molecules on a roughly one-to-one basis.

Next, the use of coupled particles is discussed.

Immune reactions classically involved mechanical effects — precipitation or agglutination — and so it was natural to attempt to provide mechanical amplification for these phenomena. Experimenters since the early 1940's have employed techniques involving attachment of immune reactants to particulate or extended solids, "carriers". With partial success, particulate solids have been used both in suspension and packed in various kinds of flow-through columns; the reactant which is originally not attached to the solid is then linked to the solid by reaction with the pre-attached homologue. (An antibody is the "immunological homologue" of the antigen which produced it, and vice versa.)

This produces various effects, depending on the size range of solid involved: for tiny particles of carrier, the reactant couples together large masses of particles; for extended carrier material, the reactant simply accumulates at the spatially-fixed location of the carrier; for spatially semi-fixed particles packed in flow-through columns, the originally-unattached reactant accumulates in the column (acting generally as if the packed particles were a porous extended carrier).

In this way, through a simple mechanical amplification of the observable effects of immune reaction, workers in immunology have been able to elucidate many important aspects of the immune reaction.

In another approach to amplifying the observable effects of immune reaction, J. H. Brewer (U.S. Pat. No. 3,074,853) and Robert W. Terry (U.S. Pat. No. 2,301,717) have described techniques for coprecipitation of suspended pigment particles with immunoprecipitates, providing a helpful color advantage in the observation of immune reactants — this technique being limited (1) to work in which a precipitate is actually formed, and being further limited in that (2) the quantity of pigment precipitated is not reliably quantitatively related to the extent of agglomeration, (3) the pigment will coprecipitate with, generally, any precipitate which forms, being almost completely non-specific to the reaction of interest, and (4), only the surfaces of such particles or clumps of particles are visible (pigments being defined as visually opaque), whereas in my invention, tracer dispersed throughout the body of the particle may be detected.

Robert W. Terry has also reported (U.S. Pat. No. 2,194,131) the use of stained antigen in assaying for antibody; his antigen happened to be Salmonella organisms.

In all of these mechanical-amplification and related schemes, and in Terry's stained-antigen technique, observation remains relatively clumsy, and the techniques remain with few exceptions the exclusive property of the careful academic worker.

The reason for this failure of the immunological "amplified clumping" approach to become a dominant analytical technique in biochemistry and medicine is clear: mere mechanical amplification is inadequate for many applications.

SUMMARY OF THE INVENTION

In accordance with the present invention, immune reactants are coupled, preferably by covalent bonding, to carrier material. For assay purposes the carrier material has associated with it a sizable quantity of tracer material, such as fluorescent tracer.

In one preferred embodiment, the carrier is in the form of microscopic particles in a fluid suspension. In other embodiments the carrier material may be used in "macro-reticular" form — that is, in the form of a microscopic particle or strand having a convoluted, open internal structure, and thus presenting extremely high surface area, per unit volume, for covalent attachment of reactants.

The carrier materials may be made to accept attachment of large quantities of reactants and, more importantly, large quantities of tracer material — so that the various difficulties mentioned in the preceding pages are obviated, as explained herebelow.

As noted in the "prior art" portion of this specification, immune-reactant attachment to particulate or other carrier material provides a means of linkage between the carrier material and the homologue of the attached reactant. Particulate carrier material is thus subject to clumping or precipitation, with extremely high specificity, as homologue molecules link two or more reactant-coated particles. The extent of this specific agglutination or precipitation then serves as a measure of the amount of homologue present. As the particles are in general much larger than the reactant molecules, detection of carrier-particle clumping is easier than direct detection of reactant clumping.

But this sort of mechanical "amplification" is limited in its ability to render assays sensitive and amenable to automation.

The benefits of the present invention transcend mere mechanical amplification, for the large quantities of tracer which may be borne by the carrier material permit increased sensitivity and thus completely automated, quantitative, photoelectric or other instrumental measurement and monitoring.

DRAWING DESCRIPTION

Greater understanding of the character and benefits of my invention may be had through reference to the following description of embodiments, and to the accompanying single drawing, which is a highly schematic representation on a microscopic scale, of certain physical relationships related to the practice of the invention.

DETAILED DESCRIPTION

In the accompanying FIGURE, carrier particles 10 and 110 are represented as suspended in a solution. Tracer molecules symbolized as "T", and also identified at 12 and 112 typically, are associated with the carrier particles — preferably, but not necessarily, by distribution generally throughout the volume of each particles, as indicated.

Molecules or other units of homologue to a substance whose assay is sought are attached, preferably by covalent chemical bonding, to the surfaces of the particles 10 and 110. The homologue units are symbolized as "H", and also are identified typically at 11 and 111.

Also suspended, or dissolved, in the solution are molecules or other units of the substance whose assay is sought, the reactant under assay, which is symbolized as "—R—" and typically identified at 13. Some units of this reactant are typically attached to one or another of the homologue units, as indicated typically at 14 and 114. As particles having such attachments drift about in the solution, reactant units —R— statistically form linkages between two particles, as indicated by reactant at 113 linking together particles 110. Depending upon concentrations and other conditions, the most favored linkage condition may be pairs as illustrated, or larger pluralities or multiplicities by attachment of further particles such as 10 to reactant at 114, or by attachment of reactant on further particles 10, as indicated at 14, to homologue 111 on already-agglomerated particles 110.

In either the pair or higher-agglomerate case, the degree of agglomeration is readily ascertained through detection of the corresponding degree of agglomeration of tracer T, the pair or higher agglomerate providing a larger "signal" pulse from correspondingly agglomerated tracer 112 than provided by the individual-particle-carried tracer 12.

The accompanying FIGURE indicates the particles 10 and 110 as generally convex everywhere about their surfaces, but the particle surface need not be so. In fact, for some applications a highly convoluted surface structure or a macro-reticular form having partially closed encaging structure, thereby permitting attachment or encagement of large quantities of homologue, is preferable; the preferred structure in other applications is a strand, of microscopic cross-section; the use of such structures is within the scope of the present invention.

The many applications in serology, and particularly human serology, are further enhanced by the low tendency of the acrylamides toward non-specific reaction, and other favorable properties of the acrylamides. However, many other carrier materials, such as other acrylic acid derivatives, agar, agarose, and other resins may be used to varying degrees of advantage within the scope of the invention.

In the earliest immunological experiments, antibody was used in clumping of bacteria, viruses and cells; red blood cells were used as carriers in some of these experiments. These biological units soon proved inconvenient for assay work, being cumbersome to maintain in usable condition and to handle, and led Paul R. Cannon and Charles E. Marshall (J. Immunol. 38 p. 365,1940) to apply synthetic carrier particles — tiny globules of collodion, which is cellulose acetate or nitrate, to immunological assays.

The collodion was little better, having a strong tendency toward unstable non-specific reaction or adsorptive binding with the immune reactants or other substances present.

Many workers have tried other carriers to which immune reactants were attached by surface adsorption. The problems here were well expressed in 1963 by A. T. Jagendorf et al. (Biochim. Biophys. Acta 78, p. 516) and A. H. Sehon (Brit. Med. Bull. 19, p. 183). The latter writer discusses the use of covalent bonding between antigens and carrier material, as an improvement relative to the adsorptive attachment.

However, even covalent bonding per se did not completely solve the problems, because of deficiencies of the then-used carrier materials themselves. This will now be pointed up with reference to the currently most widely used and commercially successful immuno-assay.

In the 1950's there was brought to light the concept of the so-called "latex test", now well-known in clinical work as a test for pregnancy, and in certain other assays for hormones.

The carrier particles here are a latex (that is, a suspension) of polystyrene. A system for producing polystyrene particles for this purpose has been patented by R. T. Fisk (U.S. Pat. No. 3,088,875), the claims being directed to a particular range of particle sizes. While the latex test is extremely widespread in use, it is so only because nothing better has until recently been available: the mechanical problems are only partially removed.

The latex particles have a tendency to stick to each other and to containers; their preparation, moreover, involves development of considerable special technique — being far from straightforward.

Their chemical properties are further aggravation. Immune reactants are generally coupled to the polystyrene by hydrophobic bonding — that is, attachment via molecular groups on the polystyrene whose affinity for water is lower than their affinity for groupings on the immune reactants — which is a very weak form of attachment, having the same general strength as immunological affinities; consequently immune reactants may be stripped away from the carrier upon reaction with their homologues. Also, techniques for attachment of many immune reactants to the latex are not available.

Finally, the latex has a variable, relatively high tendency toward non-specific attachment. This means that in tests where it can be used at all, the results of the test must be assessed statistically, because a significant (variable) amount of agglutination is almost always observed even if no homologue is present in the test solution.

In the latex pregnancy test, for example, the clumping observed in a solution derived from the patient's urine must be carefully compared visually with the clumping in a standard solution, and the relative amount of agglutination must be given a numerical rating by the visual observer. Apart from the obviously objectionable subjectivity of this method, the important fact stands out that the immunological non-specificity and variability of the latex prevents a simple yes-or-no answer to the question "Is the patient pregnant?" Instead the answer must be given in probabilistic relative terms — while there is nothing probabilistic or relative about the question. The test is in fact often inconclusive.

Thus the polystyrene particles, hydrophobically bonded to immune reactants, are relatively unsatisfactory in preparation, in use, and in measurement significance.

In related work, R. R. Porter et al. (Ann. Rev. Biochem. 31 p. 625, 1962) and Silman and Katchalski (Ann. Rev. Biochem. 35, p. 873, 1966) have reported problems with antigen covalently coupled to diazoamino polystyrene, and with poly-p-aminostyrene, respectively.

Nevertheless, the latex test, with all its drawbacks, incorporates one of the most advanced combinations of materials and bonding chemistry heretofore known in immunological applications.

In more recent work, much less widely practiced, acrylic acid derivatives have been used as immuno-carriers (Manecke et al., Pure Appln. Chem. 4 p. 507, 1962), and in another approach to the carrier technique some investigators have "encaged" immune reactants within closed structures — generally microscopic particles (Silman and Katchalski, Ann. Rev. Biochem. 35, p. 873, 1966; and Goodfriend et al., Immunochem. 6, p. 481, 1969). Inman and Dintzis (Biochem. 8, p. 4074, 1969) have described acrylamide carrier chemistry which is particularly well suited for use with the present invention.

The acrylic acid and acrylamide techniques are highly preferred to the others discussed hereabove, but the instant invention is not limited to use with these particular chemicals, others such as the polystyrene latex, other covalently-bonded carrier materials, even collodion or biological cells, being usable with the present invention — within the limitations upon their usefulness stated herein.

The acrylamide resins are advantageous both for physical and chemical properties: they can be formed into a variety of shapes of various sizes, such as microscopic globules or flecks, strands of microscopic cross-section, or thin sheets; after formation these bodies are not mutually adherent nor prone to protein adsorption; and through partial hydrolysis or hydrazinolysis they can be made amenable to covalent bonding, which is stronger than the antigen-antibody affinities and consequently provides stable attachment of carrier to antigen or antibody throughout the duration of reactions. No work is reported heretofore using these materials with associated tracer molecules, and covalently bonded to reactive substances in immunology.

Through the use of acrylamide resin — or, where loose surface convolutions are desirable, through the use of other polymers of acrylic acid or its derivatives — the particles or other structures may be made exceedingly stable, and non-mutually cohesive. They are moreover, due to their amenability to covalent bonding of immune reactants, capable of being attached to such reactants in a manner which is much stronger than immunological bonding — and thus permanent with respect to the duration of immune reactions.

Finally, there appears a further advantage, with respect to immuno-chemistry, of using the acrylamide resins: these carrier substances, because of their molecular structure, are very little prone to nonspecific reaction with immune reactants. Acrylamide is amphoteric, hydrophilic and not mutually reactive (nor reactive with proteins) — these being the three properties of proteins which render them relatively little subject to non-specific reactions. These properties are characteristic of acrylic acids also, under appropriate conditions, but not of polystyrene latex, collodion, or most other substances tried in the past as carrier materials. Thus the acrylamide in particular makes it possible to greatly reduce interference with immune monitoring due to "background" precipitation and agglutination, which are due in turn to non-specific immunological attachments involving the carrier material itself. Consequently the present invention is enhanced by the novel combination of the favorable physical, chemical and immunological properties of the acrylamide carrier and the covalent bond, thus rendering the present invention remarkably effective for many applications.

In the following paragraphs are listed various laboratory details suitable and helpful to practice of the present invention; it will be understood that other chemicals, materials and procedures may be substituted for those presented here without departing from the scope of the instant invention as defined by the appended claims.

PARTICLE MATERIALS

1. Acrylic acid — Rohm & Haas, type XE 256, 10% suspension washed three times with ten volumes of saline, resuspended to the original volume in saline and stored at 4° C.

2. Acrylamide — Calbiochem "Bio-gel" type P-150, 100 to 200 mesh. Nine grams suspended in 350 ml of 2 N hydrochloric acid, allowed to hydrolyze at room temperature (25° C) with continuous shaking for four days, then filtered. By analysis of filtrate for ammonia (0.45 mg N/ml), 8.9% of amide groupings were determined to have been hydrolyzed to carboxyl. Filtered and washed repeatedly with saline until neutral, resuspended in 150 ml saline and stored cold.

3. Agarose — Calbiochem Bio-gel type A, 0.5 M, 100 to 200 mesh, supplied in suspension and used as received.

FLUORESCENT DYES

1. Fluoresceinisothiocyanate — Calbiochem, catalog #34321.

2. $\epsilon$-dansyl-L-lysine — Calbiochem A grade, catalog #251221.

PROTEINS

1. Gamma-globulin (7s) — Calbiochem human A grade, catalog #345872, purified by dissolving to 1% in pH 8.4 buffered saline, and subjected to chromatography on a column of Bio-gel P300, monitored by UV absorption at 280 nm, collecting the second emerging peak of molecular weight about 160,000. This material concentrated to about 2.5% by ultra-filtration and "shell-frozen" in small quantities in test tubes and stored frozen.

2. Bovine albumin — purified-by-crystallization grade, Sigma Chemical Company catalog #A4378, further purified and stored in the same way as the gamma globulin. (Molecular weight about 69,000.)

3. Antibody to human 7s gamma-globulin — Calbiochem catalog #539807 "ten-fold" purified rabbit antibody, A grade.

4. Antibody to bovine serum albumin — Calbiochem catalog #539,817, "ten-fold" purified goat antibody, A grade.

OTHER CHEMICALS

1. Water-soluble carbodiimide — 1-ethyl-3-dimethylaminopropylcarbodiimide, Ott Chemical Co.

2. Hydrazine — Eastman Organic Chemicals, catalog #902.

3. Cyanogen bromide — Eastman Organic Chemicals, catalog #919.

4. Radioiodine, $I^{125}$ — sodium iodide, carrier-free, in neutral solution (available from Radiochemical Centre, Amersham, Bucks, England).

5. Chloramine-T — Eastman Organic Chemicals, catalog #1022.

6. Ethylenediamine — Eastman Organic Chemicals, catalog #1915.

RADIOACTIVE TAGGING OF ACRYLAMIDE

First react partially hydrolyzed acrylamide with tyrosine using carbodiimide activator, then iodinate that compound with radioiodine by the method of W. M. Hunter and S. C. Greenwood (Nature 194, 495, 1962). The residual carboxyl groups of the tyrosine and of the hydrolyzed polyacrylamide can then be activated with carbodiimide and coupled to the desired protein. The same protein coupling procedure can be used with the dansyl-lysine-labelled acrylic acid or acrylamide, or the fluoresceinisothiocyanate-labelled acrylamide (see paragraph 3 under "stained particles" below). There are a number of alternate procedures for coupling proteins to the various insoluble, synthetic polymer particles, as illustrated by the publication by Inman and Dintzis, or as described in numerous textbooks. See, for example, *Handbook of Experimental Immunology*, edited by D. M. Weir, F. A. Davis Co, Philadelphia, 1967; or *Methods in Immunology* by D. H. Campbell et al., W. A. Benjamin Inc., N.Y. 1964.

STAINED PARTICLES

1. Acrylic acid stained by ε-dansyl-L-lysine — Dilute the acrylic acid suspension 1:1 with saline, and adjust to pH 5.4 with 3 N Hcl. Add 10 ml to 1 ml 0.005 M ε-dansyl-lysine and 100 mg water-soluble carbodiimide. Store cold overnight, wash repeatedly with pH 9.4, 0.1 M carbonate-buffered saline until control prepared in the same way without carbodiimide is completely non-fluorescent. Wash with pH 7.4 buffered saline until pH of supernatant is about 7.6.

2. Acrylamide stained with ε-dansyl-lysine — To 5 ml hydrolyzed acrylamide suspension add 1 ml 0.005 M ε-dansyl-lysine and 50 mg water-soluble carbodiimide. Adjust pH and maintain pH at 5.0 ± 0.3 by continuous titration with 0.5 N HCl at room temperature. After two hours, wash repeatedly, first with pH 9.5, 0.1 M carbonate-buffered saline, then in pH 7.4 phosphate-buffered saline, and resuspend to 5 ml in buffered saline. Substantially all of the dye is retained on the particles.

3. Acrylamide, copolymerized with monomers containing amino groups, stained with fluoresceinisothiocyanate — To 1 ml of hydrolyzed acrylamide suspension, add 5 mg fluoresceinisothiocyanate dissolved in cold pH 9.4 carbonate-buffered saline, store cold overnight with continuous stirring, centrifuge, wash three times with ten volumes of pH 9.3 carbonate-buffered saline, and three times with ten volumes of pH 7.4 buffered saline. Substantially all of the dye is retained on the particles.

4. Agarose coupled to dansyl lysine — agarose may be activated with cyanogen bromide following the method of Cuatrecasas et al (*Proc. Nat. Acad. Sci. US* 61, 636, 1968). Add 5 ml of a suspension containing 3 ml of activated agarose in 0.1 molar carbonate buffer, pH 9.0, to 2 ml of the same buffer containing 25 mg of ε-dansyl-lysine, and hold one hour at 4° C. Quickly filter this suspension in the cold, and wash with five volumes of cold pH 9.0 buffer. Then immediately resuspend in 5 ml of a ½% solution of the protein (antibody or antigen) to which it is to be coupled, and hold 24 hours more in the cold with stirring. Wash it twice with ten volumes of cold pH 9 buffer, then with cold pH 7.4 phosphate-buffered saline until pH falls to 7.6 or below. Resuspend the precipitate in 5 ml pH 7.4 saline and store cold.

IMMUNOLOGICAL REACTIONS

Immunological reactions are carried out by mixing a few drops of a dilute suspension of the tagged and protein-coated particles with a drop or two of serum or other protein solution which it is desired to test for the presence of the homologue of the protein attached to the particle. In order to avoid inhibition of the particle coupling by an excess of the homologue, several dilutions of the solution being tested should be prepared, progressive dilutions being used until it is certain that there are no more than one or a very few molecules of homologue for each particle in the suspension. The mixture, with gentle shaking, is held at about 35° C for a few minutes to a few hours and is then examined for evidence of particle clumping. Because of the tendency of acrylamide particles to adhere to glass, the acrylamide suspension should be handled in test tubes of polystyrene, or poly-carbonate plastic, or tubes made of similar non-polar material. (Tubes having acrylamide interior surface would be ideal, but no such tubes are currently known, by me, to be on the market.) It may be found desirable to add a small quantity, 0.1% or less, of a surface-active material such as "Brij 35" (Calbiochem catalog #203711), "Tween", "Dreft" or the like to decrease the probability of non-specific clumping and adherence to container surfaces.

Clumping may be detected in one of several ways:

The suspension may be spread on a glass slide or dropped on a piece of white filter paper, or one of the special papers devised for the purpose (R. W. Terry, U.S. Pat. No. 2,301,717). This suffices to detect gross clumping visually.

Greater sensitivity can be obtained by spreading the suspension after reaction on a glass microscope slide and observing particle clumping visually with a microscope. This is facilitated, in the case of fluorescent tags, by ultraviolet excitation and ultraviolet illumination using ultraviolet transmitting glass slides and appropriate wavelength filters to discriminate against non-fluorescent scattering in the case of particles stained with fluorescent dye.

If a radioactive tracer has been used, the paper or slide may be used to prepare an autoradiograph on photographic film, by well-known techniques.

In a preferred method, the suspension after reaction is diluted and passed through a flow cell in a spectrophotofluorometer. This method may be implemented for best sensitivity and most rapid observation by use of an apparatus in which the suspension is exposed to a laser beam of wavelength appropriate to excite the dye, and monitored photoelectrically. The particles must be of substantially uniform size, for most applications, and the suspension should be so diluted that two individual particles or two particle pairs are rarely present in the cell at one time; in fact, this means that the cell should be void of particles about 9/10 of the time or more. With these conditions, a suitable circuit in the photometer can distinguish between individual and paired particles in the cell. The corresponding events can be individually counted. An example of usable instrumentation is found in U.S. Pat. No. 3,380,584 to Fulwyler.

In this way, sensitivity can be so raised that concentrations of only a few hundred molecules in the homologue solution can be detected.

An additional advantage of the fluorescent immunodetection method is that it is easily carried out automatically.

In another desirable embodiment, the immuno-agglomerate after reaction is physically separated from the fluid and any other constituents of the suspension, as for example by settling, centrifugation or filtration; the separated agglomerate is washed, and then dissolved (or melted, as for agar carrier), and the resulting fluid assayed for the fluorescent or other tag. Cellulose acetate carrier, for example, may be dissolved in acetone; acrylamide or other polymeric carrier may be made with cross-linkages which are amenable to subsequent selective severance. These embodiments are desirable when continuous-fluid-monitoring instrumentation is preferable to particle-discriminating instrumentation.

It should be noted that antigens and antibodies are commonly protein molecules of molecular weight exceeding 30,000, and having multiple "valences", that is, sites on their surfaces complementary in topology, polarity, hydrophylic or hydrophobic character, or perhaps in other ways to their immunologic homologs. Such sites account for specific combining affinity for their homologs. Nevertheless, many substances, including many that are normally non-antigenic may be modified by chemical attachment to proteins so that they then become antigenic. Such non-antigenic substances are often called haptens.

When coupled to proteins in this way haptens can stimulate the formation of antibodies having specific binding affinities not only for the hapten-protein molecules, but also for the haptens themselves.

The number of substances that have been found to act as haptens is so large and varied that it is not an exaggeration to say that almost any molecular species, organic or inorganic, large or small, may act in this way if suitable conditions are sought for preparing antigens from it and appropriate tests made for its immunological binding power.

Since haptens often are immunologically monovalent, and thus incapable of coupling antibody-coated particles together or of binding them to a stationary surface, no matter how firmly they may be bound to antibody attached to the surfaces of the particles or stationary solid, a different but well known technique is usually used to detect their affinity for their respective specific homologs. This is a technique called competitive binding. To illustrate, and to show how this technique may be used with the particles of my invention, labeled particles may be immunologically bound to a fixed surface, such as the wall of a test-tube, using the hapten-protein molecules (which ordinarily carry many hapten molecules per molecule of protein and thus are multi-valent) as the reactant 113 of FIG. 1.

On adding a solution to be analysed for its hapten content to a surface prepared in this way, the hapten competes for the binding sites on the anti-hapten antibodies with which the surface and the particles are coated, freeing the immunologic link therebetween and allowing the particles to become suspended in the solution. They may then be detected in suspension, or their diminution on the surface may be measured, by means of the label or "tracer" they carry, and the presence and amount of hapten in the solution may be inferred thereby.

It should also be noted that as is well known, antibody gamma globulin molecules can be broken into certain fragments by the action of enzymes or chemical reagents that attack disulfide linkages. Some of these fragments have their antigen-binding affinity preserved almost completely, others will bind but not precipitate antigen (in an analogous way to that in which many haptens bind but do not precipitate antibody). Some of the separate fragments also occur naturally under certain circumstances.

In studying the antigen-binding affinity of these fragments, methods similar to those used for studying hapten affinity for antibody have been used.

It is clear that the tagged particles of my invention may be used to advantage to detect haptens or fragments of antibody (or antigent), both for scientific study and clinical application. For this reason I use the phrase, "..antibodies, antigens, portions and equivalents thereof..." to characterize these very diverse substances.

I claim:

1. A reagent for use in immuno-assay, comprising
   (a) water suspendible particles selected from the group consisting of acrylamide, acrylic acid and polyacrylic acid and derivatives thereof, polymers of styrene and derivatives thereof, agar, agarose, and cellulose acetate, each particle containing a plurality of radioactive tracer atoms distributed generally throughout the volume of the particle,
   (b) the particles having coupled thereto a multiplicity of molecules of a substance selected from the group consisting of antibodies, antigens and portions and equivalents thereof.

2. The reagent of claim 1 wherein the particles are porous to the tracer molecules or atoms.

3. A reagent for use in immuno-assay, comprising
   (a) water suspendible particles selected from the group consisting of acrylamide, acrylic acid and polyacrylic acid and derivatives thereof, polymers of styrene and derivatives thereof, agar, agarose, and cellulose acetate, each particle containing a plurality of fluorescent or other tracer molecules or atoms distributed generally throughout the volume of the particle,
   (b) the particles having coupled thereto a multiplicity of molecules of a substance selected from the group consisting of antibodies, antigens and portions and equivalents thereof.

4. The reagent of claim 3 wherein the particles are porous to the tracer molecules or atoms.

5. The process for assaying an aqueous sample for a particular reactant selected from the group consisting of antibodies, antigens, portions and equivalents thereof, that includes
   (a) providing multiple water suspendible polymeric particles, and labeling each particle within the volume thereof with a multiplicity of tracer molecules,
   (b) coupling to said particles a multiplicity of molecules of a substance selected from the group consisting of antibodies, antigens and portions and equivalents thereof,
   (c) mixing the suspension of particles with the aqueous sample to produce linking of multiple particles with units of reactant, thereby to form agglomerate,
   (d) detecting tracer concentration in the agglomerate, or in the suspending medium free of agglomerate to thereby determine the amount of reactant in the mix, and
   (e) using the known quantity of sample and the detected amount of reactant in the mix to compute the concentration of reactant in the sample.

6. The process of claim 5 includes also carrying out the steps of the process using a sample containing a known concentration of the reactant, and using the resultant detected tracer concentrations in the agglomerate or the suspending medium free of agglomerate as a calibration value in said computing step.

7. The process of assaying an aqueous sample for a particular reactant selected from the group consisting of antibodies, antigens, portions and equivalents thereof, and wherein tracer-sensitive instrumentation is employed, that includes
   (a) providing multiple water suspendible polymeric particles, and labeling each particle within the volume thereof with a multiplicity of tracer molecules,
   (b) coupling to each particle a multiplicity of molecules of a substance selected from the group consisting of antibodies, antigens and portions and equivalents thereof,
   (c) mixing the suspension of particles with the aqueous sample to produce linking of multiple particles with units of reactant, thereby to form agglomerate, and
   (d) detecting tracer concentration in the agglomerate, or in the suspending medium free of agglomerate to thereby determine the amount of reactant in the mix, said determining step being carried out by exposing said agglomerate or said suspending medium free of agglomerate to said instrumentation sensitive to the tracer, and also operating said instrumentation.

8. The process of claim 7 wherein said instrumentation comprises a fluorometer including a flow cell, said determining step includes diluting the mix or said suspending medium free of agglomerate to form a dilution, and said exposing step includes passing the dilution through the flow cell.

9. The process of claim 7 wherein the operation of said instrumentation is carried out to distinguish between single particles and particle pairs or clumps.

10. The process of claim 5 wherein said particles are meltable, and including the step of separating the agglomerate and melting the particles after separating said agglomerate.

11. The process of claim 10 wherein the polymeric particles have cross-links characterized as severable in response to said melting step.

12. The process of claim 10 wherein the particles consist of agar.

13. A method for providing increased sensitivity in immunologic tests for a particular reactant in an aqueous sample, the reactant having multiple immunologic valences and selected from the group consisting of antibodies, antigens, portions and equivalents thereof, that includes:
(a) providing an extended carrier surface, and coupling to said surface a multiplicity of molecules of a first substance selected from the group consisting of antibodies, antigens and portions and equivalents thereof, the first substance being an immunologic homologue to said reactant,
(b) providing multiple water suspendible polymeric particles labeled within the volumes thereof with a multiplicity of tracer molecules, the particles having coupled thereto a multiplicity of molecules of a second substance selected from the group consisting of antibodies, antigens and portions and equivalents thereof, by reacting the particles with said molecules in aqueous solution in which the particles are suspended, said second substance being an immunological homologue to said reactant,
(c) exposing the carrier surface of said sample to produce linking of said first substance molecules with units of the reactant,
(d) exposing the carrier surface to said suspension of polymeric particles to produce linking of said second substance molecules with units of reactant previously linked to said carrier surface as aforesaid, and
(e) detecting the extent of tracer adherence, via the reactant, to the extended carrier surface.

14. The method of claim 13 wherein said detecting step includes counting the adhered particles.

15. The method of claim 13 wherein said detecting step is facilitated by liquifying the adhered particles.

16. The method of claim 13 wherein the first and second substances are the same.

17. The method of claim 13 wherein said detecting step includes quantitatively determining the amount of tracer in the adhered particles.

18. The method of claim 13 wherein said determining step includes of quantitatively determining the amount tracer in the non-adhered particles.

19. A method for providing increased sensitivity in immunologic tests for a particular reactant in an aqueous sample, the reactant selected from the group consisting of antibodies, antigens, portions and equivalents thereof, that includes:
(a) providing an extended carrier surface, and coupling to said surface a multiplicity of molecules of a first substance selected from the group consisting of antibodies, antigens and portions and equivalents thereof, the first substance being an immunologic homologue to said reactant,
(b) providing multiple water suspendible polymeric particles labeled within the volumes thereof with a multiplicity of tracer molecules, the particles having coupled thereto a multiplicity of molecules of a second substance selected from the group consisting of antibodies, antigens and portions and equivalents thereof, by reacting the particles with said molecules in aqueous solution in which the particles are suspended, said second substance being an immunological homologue to said first substance,
(c) exposing the carrier surface to said suspension of polymeric particles, to produce linking of said first substance molecules with units of second substance, thereby binding them to the surface,
(d) exposing the so-prepared carrier surface to said sample to produce linking of said particular reactant molecules with units of said first substance previously bound to said carrier surface as aforesaid,
(e) thereby displacing said particles from said surface, causing them to become resuspended, and
(f) detecting the extent of resuspension of the particles by observing either the tracer appearing in the suspension of particles or the diminution of tracer remaining adherent to the extended carrier surface.

20. A reagent for use in immuno-assay, comprising
(a) water suspendible polymeric particles, each particle being labeled generally throughout its volume with a multiplicity of tracer molecules, and
(b) each particle having coupled to it a multiplicity of molecules of a substance selected from the group consisting of antibodies, antigens and portions and equivalents thereof, the particles being dispersed in aqueous solution.

21. A reagent for use in immuno-assay, comprising
(a) water suspendible polymeric particles, each particle being labeled generally throughout its volume with a multiplicity of tracer molecules, and
(b) each particle having coupled to it a multiplicity of molecules of a substance selected from the group consisting of antibodies, antigens and portions and equivalents thereof.

* * * * *